(12) United States Patent
Suzuki et al.

(10) Patent No.: US 10,807,930 B2
(45) Date of Patent: Oct. 20, 2020

(54) METHOD FOR PRODUCING GAMMA, DELTA-UNSATURATED ALCOHOL

(71) Applicant: KURARAY CO., LTD., Kurashiki-shi (JP)

(72) Inventors: Yutaka Suzuki, Chiyoda-ku (JP); Masaki Shimizu, Kamisu (JP)

(73) Assignee: KURARAY CO., LTD., Kurashiki-shi (JP)

( * ) Notice: Subject to any disclaimer, the term of this patent is extended or adjusted under 35 U.S.C. 154(b) by 0 days.

(21) Appl. No.: 16/479,743

(22) PCT Filed: Jan. 26, 2018

(86) PCT No.: PCT/JP2018/002577
§ 371 (c)(1),
(2) Date: Jul. 22, 2019

(87) PCT Pub. No.: WO2018/143104
PCT Pub. Date: Aug. 9, 2018

(65) Prior Publication Data
US 2020/0062680 A1   Feb. 27, 2020

(30) Foreign Application Priority Data
Jan. 31, 2017 (JP) .................. 2017-015826

(51) Int. Cl.
  *C07C 29/38* (2006.01)
  *C07C 33/025* (2006.01)
(52) U.S. Cl.
  CPC ............ *C07C 29/38* (2013.01); *C07C 33/025* (2013.01)
(58) Field of Classification Search
  CPC .............................. C07C 29/38; C07C 33/025
  See application file for complete search history.

(56) References Cited

U.S. PATENT DOCUMENTS

| 2,335,027 A | 11/1943 | Ritter et al. |
| 4,110,403 A | 8/1978 | Ichikawa et al. |
| 2017/0197895 A1 | 7/2017 | Suzuki |

FOREIGN PATENT DOCUMENTS

| CN | 104130107 A | 11/2014 |
| CN | 105439823 A | 3/2016 |
| JP | 47-47362 B | 11/1972 |
| JP | 50-88009 | 7/1975 |
| JP | 50-111003 | 9/1975 |
| JP | 51-39616 | 4/1976 |
| JP | 7-285899 A | 10/1995 |
| WO | WO 02/051776 A2 | 7/2002 |
| WO | WO 2004/058670 A1 | 7/2004 |
| WO | WO 2015/186699 A1 | 12/2015 |

OTHER PUBLICATIONS

JP 3563105 B2, Katsushi et al, production of gamma-delta unsaturated alcohol (machine English translation), 2004.*
International Search Report dated Mar. 6, 2018 in PCT/JP2018/002577 filed on Jan. 26, 2018.
Babers, F. H. et al., Journal of the American Chemical Society (J. Am. Chem. Soc.), vol. 77, 1955, pp. 4666-4668.

* cited by examiner

*Primary Examiner* — Jafar F Parsa
(74) *Attorney, Agent, or Firm* — Oblon, McClelland, Maier & Neustadt, L.L.P.

(57) ABSTRACT

A method for producing a γ,δ-unsaturated alcohol of formula (2):

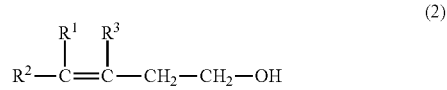

wherein $R^1$ to $R^3$ each independently represent a hydrogen atom, an alkyl group having 1 to 10 carbon atoms and optionally substituted with a hydroxy group, an alkenyl group having 2 to 10 carbon atoms and optionally substituted with a hydroxy group, or an aryl group having 6 to 12 carbon atoms and optionally substituted with a hydroxy group, provided that $R^1$ and $R^3$ may bond to each other to form a ring, through a reaction of an α-olefin of formula (1) and formaldehyde under a heating condition:

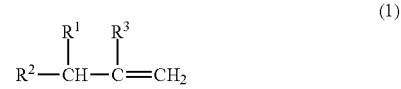

the method including a step of bringing the α-olefin into contact with an aqueous formaldehyde solution in the presence of an alcohol having 3 to 10 carbon atoms, with the aqueous formaldehyde solution being subjected to preheating at 30 to 220° C. before the step.

11 Claims, No Drawings

METHOD FOR PRODUCING GAMMA, DELTA-UNSATURATED ALCOHOL

TECHNICAL FIELD

The present invention relates to a method for producing a γ,δ-unsaturated alcohol.

BACKGROUND ART

A γ,δ-unsaturated alcohol has a double bond and a hydroxy group in the molecule thereof, and by converting the respective functional groups, it can be converted into a variety of organic compounds. Therefore, the γ,δ-unsaturated alcohol is an extremely useful compound in the field of organic synthetic chemistry.

As one of production methods of the foregoing γ,δ-unsaturated alcohol, there is known a method of subjecting an α-olefin of every sort and kind and an aldehyde to thermal reaction in the absence of a catalyst. For example, PTL 1 and NPL 1 disclose a method of allowing an α-olefin and an aldehyde to react with each other at 100 to 250° C. for 2 to 16 hours under a high pressure of 200 atm (20.3 MPa) or more. However, according to this method, the yield is merely at most 31% since large quantities of high-boiling point side products are produced.

PTL 2 discloses a method of reacting an α-olefin and an aldehyde at a temperature falling within a range of 235 to 400° C. and under a pressure condition of 1,000 atmospheres or less to produce a targeted γ,δ-unsaturated alcohol at a relatively good yield, recommending to carry out the reaction in the coexistence of a basic compound such as ammonia or hexamethylenetetramine. PTL 3 discloses a method of reacting an α-olefin and an aldehyde in the coexistence of a phosphate at a temperature falling within a range of −20 to 320° C. under a pressure condition of 100 to 250 atmospheres to produce a targeted γ,δ-unsaturated alcohol at a relatively good yield. However, judging from the description of examples thereof, these methods are problematic in that a sufficient industrial yield could not be attained in the absence of a basic compound.

PTL 4 describes a method of using a solvent of an alcohol having 3 to 10 carbon atoms in an amount of 2 to 20 molar times the amount of formaldehyde in a formaldehyde solution and reacting at 150 to 350° C. under a pressure of 30 to 500 atmosphere to give a product at a selectivity of at most 91%. However, for obtaining a satisfactory yield in the method, the amount of the α-olefin to be used must be 10 molar times the amount of the aldehyde, and therefore the method is problematic in that the industrial production yield is low.

PTL 5 discloses a method of reacting an α-olefin and an anhydrous formaldehyde at a temperature falling within a range of 200 to 300° C. under a reaction condition of 5 to 80 atmospheres to produce a targeted γ,δ-unsaturated alcohol at a relatively good yield. PTL 6 discloses a method of reacting an α-olefin and formaldehyde in a molar ratio of 2 or more at a temperature falling within a range of 150 to 400° C. to produce a γ,δ-unsaturated alcohol at a high yield. Further, PTL 7 discloses, as an improved method of PTL 6, a method of adding an aldehyde preheated at a temperature of 80 to 150° C. to the reaction system.

However, in these methods, it is said that aldehyde is used after removal of water therefrom, and therefore in these methods, an inexpensive aqueous formaldehyde solution could not be used. In addition, judging from the description of examples thereof, the method of PTL 7 uses a paraformaldehyde, and nothing is disclosed relating to use of an aqueous formaldehyde solution.

PTL 8 describes a method of preheating a formaldehyde methanol hemiacetal form at a temperature falling within a range of 280 to 350° C. and under a pressure condition of 12 to 18 MPa, and rapidly mixing it with an isobutylene also preheated under the same condition to produce 3-methyl-3-buten-1-ol at a high yield. However, the method is problematic in that, when a formaldehyde solution is heated at 230° C. or higher, the formaldehyde becomes unstable and therefore the yield of the targeted γ,δ-unsaturated alcohol lowers. PTL 9 describes a method of preheating a formaldehyde methanol solution at a temperature falling within a range of 150 to 200° C. and under a pressure condition of 15 to 22 MPa, and spraying it onto an isobutylene preheated at a temperature falling within a range of 220 to 300° C. and under a pressure condition of 15 to 22 MPa to produce 3-methyl-3-buten-1-ol at a high yield. However, according to the disclosure of Comparative Example 2 in PTL 4, the reaction yield of the γ,δ-unsaturated alcohol in the case of using methanol as a reaction solvent is 38.0% and is low. Further, methanol is a harmful compound and therefore provides a problem of waste treatment after the reaction.

CITATION LIST

Patent Literature

PTL 1: U.S. Pat. No. 2,335,027
PTL 2: JP 47-47362 B
PTL 3: WO 02/051776 A
PTL 4: JP 7-285899 A
PTL 5: WO 2004/058670 A
PTL 6: JP 50-88009 A
PTL 7: JP 51-39616 A
PTL 8: Chinese Patent Application Publication No. 104130107
PTL 9: Chinese Patent Application Publication No. 105439823

Non-Patent Literature

NPL 1: Journal of the American Chemical Society (J. Am. Chem. Soc.), Vol. 77, p. 4666, 1955

SUMMARY OF INVENTION

Technical Problem

As described above, the methods have various problem in industrial practicability thereof. Given the situation, an object of the present invention is to provide a method for producing a γ,δ-unsaturated alcohol at high yield and good productivity.

Solution to Problem

According to the present invention, the above-mentioned object can be attained by the following [1] to [9].

[1] A method for producing a γ,δ-unsaturated alcohol represented by the following general formula (2):

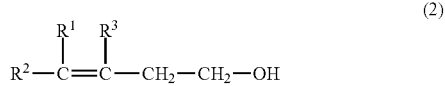

wherein $R^1$ to $R^3$ each independently represent a hydrogen atom, an alkyl group having 1 to 10 carbon atoms and optionally substituted with a hydroxy group, an alkenyl group having 2 to 10 carbon atoms and optionally substituted with a hydroxy group, or an aryl group having 6 to 12 carbon atoms and optionally substituted with a hydroxy group, provided that $R^1$ and $R^3$ may bond to each other to form a ring, through a reaction of an α-olefin represented by the following general formula (1) and formaldehyde under a heating condition:

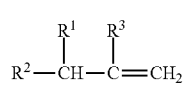

(1)

wherein $R^1$ to $R^3$ are as defined above:
the method including a step of bringing the α-olefin into contact with an aqueous formaldehyde solution in the presence of an alcohol having 3 to 10 carbon atoms, with the aqueous formaldehyde solution being subjected to preheating at 30 to 220° C. before the step.

[2] The production method according to the above [1], wherein the time for the preheating is less than 30 minutes.

[3] The production method according to the above [1] or [2], wherein the aqueous formaldehyde solution is subjected to preheating at 70 to 190° C.

[4] The production method according to any one of the above [1] to [3], wherein the amount of the alcohol having 3 to 10 carbon atoms to be used is from 0.5 to 20 mol relative to 1 mol of formaldehyde in the aqueous formaldehyde solution.

[5] The production method according to any one of the above [1] to [4], wherein the temperature during the reaction is from 150 to 350° C.

[6] The production method according to any one of the above [1] to [5], wherein in the step, a mixture of the α-olefin and the alcohol having 3 to 10 carbon atoms is brought into contact with the aqueous formaldehyde solution.

[7] The production method according to the above [6], wherein before the step of bringing the α-olefin into contact with the aqueous formaldehyde solution, the mixture is subjected to preheating at 70° C. or higher.

[8] The production method according to the above [7], wherein the aqueous formaldehyde solution is subjected to preheating at 70 to 190° C., and the mixture is subjected to preheating at 70 to 380° C.

[9] The production method according to any one of the above [1] to [8], wherein the reaction is carried out in the absence of a catalyst.

Advantageous Effects of Invention

In accordance with the present invention, a γ,δ-unsaturated alcohol can be produced at high yield and good productivity. A γ,δ-unsaturated alcohol can be a raw material or an intermediate for various organic compounds, and 3-methyl-3-buten-1-ol is especially useful as a precursor for isoprene and a raw material or an intermediate for medicines and perfumes.

DESCRIPTION OF EMBODIMENTS

In this description, the restrictive wording with "being preferred" can be arbitrarily selected, and a combination of restrictive wordings with "being preferred" may be said to be more preferred.

[Method for Producing γ,δ-Unsaturated Alcohol]

The method for producing a γ,δ-unsaturated alcohol of the present invention (hereinafter this may be simply referred to as "the production method of the present invention") is a method for producing a γ,δ-unsaturated alcohol represented by the following general formula (2):

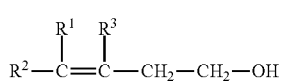

(2)

wherein $R^1$ to $R^3$ each independently represent a hydrogen atom, an alkyl group having 1 to 10 carbon atoms and optionally substituted with a hydroxy group, an alkenyl group having 2 to 10 carbon atoms and optionally substituted with a hydroxy group, or an aryl group having 6 to 12 carbon atoms and optionally substituted with a hydroxy group, provided that $R^1$ and $R^3$ may bond to each other to form a ring, through a reaction of an α-olefin represented by the following general formula (1) and formaldehyde under a heating condition:

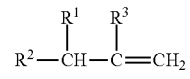

(1)

wherein $R^1$ to $R^3$ are as defined above, and the method includes a step of bringing the α-olefin into contact with an aqueous formaldehyde solution in the presence of an alcohol having 3 to 10 carbon atoms, with the aqueous formaldehyde solution being subjected to preheating at 30 to 220° C. before the step.

According to the production method of the present invention, a γ,δ-unsaturated alcohol represented by the general formula (2) can be produced at high yield and good productivity.

In the present invention, preferably, the reaction between the α-olefin represented by the general formula (1) and formaldehyde is carried out in the absence of a catalyst. The catalyst as referred to herein means a conventionally-known catalyst usable in an addition reaction of an α-olefin and formaldehyde, and examples thereof include a basic compound and a phosphorus-containing compound.

<α-Olefin>

The α-olefin for use in the present invention is represented by the following general formula (1):

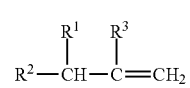

(1)

wherein $R^1$ to $R^3$ each independently represent a hydrogen atom, an alkyl group having 1 to 10 carbon atoms and optionally substituted with a hydroxy group, an alkenyl group having 2 to 10 carbon atoms and optionally substituted with a hydroxy group, or an aryl group having 6 to 12 carbon atoms and optionally substituted with a hydroxy group, provided that $R^1$ and $R^3$ may bond to each other to form a ring.

In the following description, the α-olefin represented by the general formula (1) may be simply referred to as "α-olefin".

Examples of the aforementioned alkyl group having 1 to 10 carbon atoms include a methyl group, an ethyl group, various propyl groups (the term "various" expresses that a linear-chain group and various branched-chain groups are included; hereinafter the same), various butyl groups, various hexyl groups, various octyl groups, and various decyl groups. Above all, an alkyl group having 1 to 6 carbon atoms is preferred, an alkyl group having 1 to 3 carbon atoms is more preferred, and a methyl group is still more preferred. As the hydroxy group-substituted alkyl group having 1 to 10 carbon atoms, it is not particularly limited so long as it is one in which one or more hydrogen atoms in the alkyl group having 1 to 10 carbon atoms is/are substituted with hydroxy group(s), and the number of the hydroxy group(s) is preferably 1 to 3, and more preferably 1. Examples of the hydroxy group-substituted alkyl group having 1 to 10 carbon atoms include a methylol group, a 2-hydroxyethyl group, and a 4-hydroxy-n-butyl group. The carbon number of the hydroxy group-substituted alkyl group having 1 to 10 carbon atoms is preferably 1 to 6, more preferably 1 to 3, and still more preferably 1.

Examples of the aforementioned alkenyl group having 2 to 10 carbon atoms include a vinyl group, an allyl group, an isopropenyl group, a 5-hexen-1-yl group, a 3-hexen-1-yl group, a 7-octen-1-yl group, a 5-octen-1-yl group, a 9-decen-1-yl group, and a 7-decen-1-yl group. Above all, an alkenyl group having 2 to 6 carbon atoms is preferred, and an alkenyl group having 2 to 4 carbon atoms is more preferred. As the hydroxy group-substituted alkenyl group having 2 to 10 carbon atoms, it is not particularly limited so long as it is one in which one or more hydrogen atoms in the alkenyl group having 2 to 10 carbon atoms is/are substituted with hydroxy group(s), and the number of the hydroxy group(s) is preferably 1 to 3, and more preferably 1. Examples of the hydroxy group-substituted alkenyl group having 2 to 10 carbon atoms include a 2-hydroxy-5-hexen-1-yl group, and a 2-hydroxy-5-octen-1-yl group. The carbon number of the hydroxy group-substituted alkenyl group having 2 to 10 carbon atoms is preferably 3 to 10, more preferably 3 to 6, and still more preferably 3 to 4.

Examples of the aforementioned aryl group having 6 to 12 carbon atoms include a phenyl group, a tolyl group, an ethylphenyl group, an isopropylphenyl group, a xylyl group, a trimethylphenyl group, a naphthyl group, and a biphenylyl group. Above all, an aryl group having 6 to 10 carbon atoms is preferred. As the hydroxy group-substituted aryl group having 6 to 12 carbon atoms, it is not particularly limited so long as it is one in which one or more hydrogen atoms in the aryl group having 6 to 10 carbon atoms is/are substituted with hydroxy group(s), and the number of the hydroxy group(s) is preferably 1 to 3, and more preferably 1. Examples of the hydroxy group-substituted aryl group having 6 to 12 carbon atoms include a 2-hydroxyphenyl group, a 3-hydroxyphenyl group, a 4-hydroxyphenyl group, a 2-hydroxy-1-naphthyl group, a 3-hydroxy-1-naphthyl group, a 4-hydroxy-1-naphthyl group, an 8-hydroxy-1-naphthyl group, and a 1-hydroxy-2-naphthyl group. The carbon number of the hydroxy group-substituted aryl group having 6 to 12 carbon atoms is preferably 6 to 10.

As the ring in the case where $R^1$ and $R^3$ bond to each other to form a ring, a saturated aliphatic ring having 5 to 10 carbon atoms, such as cyclopentane (5-membered ring), cyclohexane (6-membered ring), cyclooctane (8-membered ring) and cyclodecane (10-membered ring), is preferably exemplified. Above all, the ring is preferably cyclohexane Of those, from the viewpoint of decreasing a by-product, $R^3$ is preferably an alkyl group having 1 to 10 carbon atoms, more preferably an alkyl group having 1 to 6 carbon atoms, further more preferably an alkyl group having 1 to 3 carbon atoms, and especially preferably a methyl group. In addition, preferably, at least one of $R^1$ and $R^2$ is a hydrogen atom. It is more preferred that at least one of $R^1$ and $R^2$ is a hydrogen atom, and $R^3$ is an alkyl group having 1 to 10 carbon atoms (still more preferably an alkyl group having 1 to 6 carbon atoms, further more preferably an alkyl group having 1 to 3 carbon atoms, and especially preferably a methyl group). It is especially preferred that all of $R^1$ and $R^2$ are hydrogen atoms, and $R^3$ is an alkyl group having 1 to 10 carbon atoms (more preferably an alkyl group having 1 to 6 carbon atoms, further more preferably an alkyl group having 1 to 3 carbon atoms, and especially preferably a methyl group). More preferred examples of the respective groups are the same as described above.

Specific examples of a combination of $R^1$, $R^2$, and $R^3$ include:

(1) a combination in which all of $R^1$, $R^2$, and $R^3$ are a hydrogen atom [α-olefin=propylene], (2) a combination in which $R^1$ and $R^2$ are hydrogen atoms, and $R^3$ is an alkyl group having 1 to 10 carbon atom [α-olefin=isobutene ($R^3$ is a methyl group), etc.], (3) a combination in which at least one of $R^1$ and $R^2$ is a hydrogen atom (preferably the other is an alkyl group having 1 to 10 carbon atoms), and $R^3$ is an alkyl group having 1 to 10 carbon atoms [α-olefin=2-methyl-1-butene, 2-methyl-1-pentene, 2-methyl-1-hexene, 2-methyl-1-heptene, 2-methyl-1-octene, etc.], (4) a combination in which all of $R^1$, $R^2$, and $R^3$ are alkyl groups each having 1 to 10 carbon atoms [α-olefin=2,3-dimethyl-1-butene, etc.], (5) a combination in which $R^1$ and $R^2$ are hydrogen atoms, and $R^3$ is an aryl group having 6 to 10 carbon atoms [α-olefin=α-methylstyrene, etc.], (6) a combination in which $R^2$ is a hydrogen atom, and $R^1$ and $R^3$ bond to each other to form a ring [α-olefin=methylenecyclohexane, etc.], (7) a combination in which one of $R^1$ and $R^2$ is a hydrogen atom, the other being a hydroxy group-substituted alkyl group having 1 to 10 carbon atoms, and $R^3$ is a hydrogen atom [α-olefin=3-buten-1-ol, etc.], (8) a combination in which one of $R^1$ and $R^2$ is a hydrogen atom, the other being a hydroxy group-substituted alkyl group having 1 to 10 carbon atoms, and $R^3$ is an alkyl group having 1 to 10 carbon atoms [α-olefin=3-methyl-3-buten-1-ol, etc.].

In the case where at least one of $R^1$, $R^2$, and $R^3$ represents an alkenyl group or an aryl group, there might be a case where a material resulting from reaction of the alkenyl group or aryl group with formaldehyde is formed. As the α-olefin, not only a single compound but also a mixture of the above-exemplified compounds may also be used.

The amount of the α-olefin used is preferably 1 to 50 mol, more preferably 3 to 30 mol, and still more preferably 3 to 15 mol per mol of formaldehyde. When the amount of the α-olefin used is 1 mol or more per mol of formaldehyde, the selectivity of the targeted γ,δ-unsaturated alcohol is improved; whereas when it is 50 mol or less, equipment required for recovery of the α-olefin becomes small, so that not only the industrial value is improved, but also there is a tendency that the volumetric efficiency is improved, and the productivity is improved.

<Aqueous Formaldehyde Solution>

The aqueous formaldehyde solution (formalin) is, for example, an aqueous formaldehyde solution having a concentration of 10 to 80% by mass. The aqueous formaldehyde solution is preferred since it is easily available and is easy to handle. From the viewpoint of volume efficiency, the concentration of formaldehyde in the aqueous solution is preferably higher. On the other hand, from the viewpoint of preventing paraformaldehyde from depositing in the aqueous solution, the formaldehyde concentration in the aqueous solution is preferably not too high. From these viewpoints, the concentration of the aqueous formaldehyde solution is preferably 10 to 70% by mass, more preferably 20 to 65% by mass, even more preferably 30 to 60% by mass, and further more preferably 40 to 60% by mass.

Within a range not detracting from the effects of the present invention, the aqueous formaldehyde solution may contain methanol or the like generally added thereto as a stabilizer for formalin. However, the content thereof is preferably 10% by mass or less in the aqueous solution.

<Alcohol Having 3 to 10 Carbon Atoms>

The production method of the present invention includes a step of bringing the α-olefin into contact with an aqueous formaldehyde solution in the presence of an alcohol having 3 to 10 carbon atoms. The alcohol having 3 to 10 carbon atoms can uniformly dissolve the α-olefin and formaldehyde and is therefore favorable as a reaction solvent in the reaction of the α-olefin and formaldehyde.

Examples of the alcohol having 3 to 10 carbon atoms include, though not limited thereto, an acyclic aliphatic alcohol such as n-propanol, isopropyl alcohol, n-butanol, tert-butyl alcohol, isobutyl alcohol, sec-butyl alcohol, n-pentanol, 3-methyl-1-butanol, 2-methyl-2-butanol, hexanol, 3-methyl-3-pentanol, 2-ethylhexanol, heptanol, octanol, isooctanol, 2-ethyl-1-hexanol, nonanol and decanol; an alicyclic alcohol such as cyclopentanol, cyclohexanol, methylcyclohexanol, cycloheptanol, cyclooctanol and cyclodecanol; and an aromatic alcohol such as benzyl alcohol.

One alone of the above alcohols may be used, or two or more kinds thereof may be used in combination.

From the viewpoint of uniformly dissolving the α-olefin and formaldehyde, the carbon number of the alcohol is preferably 3 to 8, more preferably 3 to 6, even more preferably 3 to 5.

Also from the viewpoint of uniformly dissolving the α-olefin and formaldehyde, among the alcohol having 3 to 10 carbon atoms, an acyclic aliphatic alcohol is preferred; one or more selected from the group consisting of isopropyl alcohol, isobutyl alcohol, sec-butyl alcohol, tert-butyl alcohol, 3-methyl-1-butanol and 2-methyl-2-butanol are more preferred; and tert-butyl alcohol is even more preferred.

The amount of the alcohol having 3 to 10 carbon atoms to be used in this reaction is preferably 0.5 to 20 mol relative to one mol of formaldehyde in the aqueous formaldehyde solution, more preferably 1 to 10 mol, and even more preferably 1 to 5 mol. When the amount of the alcohol having 3 to 10 carbon atoms used is 0.5 mol or more relative to one mol of formaldehyde, a byproduct, alkyl-m-dioxane can be prevented from being produced; and when the amount is 20 mol or less, the scale of distillation equipments for separation and collection as well as the amount of steam and power to be the heat source can be simplified, therefore tending to improve the industrial value of the invention.

<Preheating>

In the present invention, before the step of bringing the α-olefin into contact with an aqueous formaldehyde solution in the presence of an alcohol having 3 to 10 carbon atoms (hereinafter this may be simply referred to as "contact step"), the aqueous formaldehyde solution is subjected to preheating at 30 to 220° C. By preheating the system at the temperature, paraformaldehyde could hardly precipitate even in the case where a high-concentration aqueous formaldehyde solution is used, and the reaction stability therefore improves. In addition, formaldehyde decomposition can also be retarded, the γ,δ-unsaturated alcohol can be produced at a high yield and the productivity thereof can therefore increase.

The preheating temperature of the aqueous formaldehyde solution falls within a range of 30 to 220° C. When the preheating temperature is lower than 30° C., paraformaldehyde may readily precipitate in the case where a high-concentration aqueous formaldehyde solution is used for improving the volume efficiency, therefore making it difficult to drive the production facilities. Preferably, the reaction of the α-olefin and formaldehyde is carried out at a high temperature of 150° C. or higher and for a short period of time. The reason is because short-time reaction is advantageous for preventing formaldehyde decomposition and improving productivity, and high-temperature reaction is advantageous for increasing the formaldehyde conversion ratio and the reaction selectivity. However, when the preheating temperature of the aqueous formaldehyde solution is lower than 30° C., it is unfavorable since the time to be taken to reach the targeted reaction temperature in the reaction system after the contact of the α-olefin and the aqueous formaldehyde solution may be long.

On the other hand, when the preheating temperature of the aqueous formaldehyde solution is higher than 220° C., formaldehyde decomposition reaction is promoted so that the yield of the targeted γ,δ-unsaturated alcohol may tend to lower.

The preheating temperature of the aqueous formaldehyde solution is, from the viewpoint of preventing paraformaldehyde from precipitating in the aqueous formaldehyde solution, from the viewpoint of increasing the conversion ratio and the reaction selectivity of formaldehyde and from the viewpoint of improving productivity, preferably 40° C. or higher, more preferably 60° C. or higher, even more preferably 70° C. or higher, still more preferably 80° C. or higher, and from the viewpoint of preventing formaldehyde from decomposing to increase the yield of the product, the preheating temperature is preferably 190° C. or lower, more preferably 160° C. or lower, and even more preferably 155° C. or lower.

The preheating time for the aqueous formaldehyde solution may be appropriately selected depending on the reaction scale, but is, from the viewpoint of preventing decomposition of formaldehyde and improving productivity, preferably as short as possible. From this viewpoint, the preheating time is preferably less than 30 minutes, more preferably 20 minutes or less, even more preferably 15 minutes or less, and still more preferably 10 minutes or less. Also preferably, the preheating time is 10 seconds or more, more preferably 1 minute or more, and even more preferably 2 minutes or more.

The preheating time for the aqueous formaldehyde solution in this description indicates the time from the start of heating the aqueous formaldehyde solution to the time at which the solution is brought into contact with α-olefin. In the case where a continuous system is employed for the production method of the present invention, the residence time for the aqueous formaldehyde solution in a preheating tube kept at a predetermined preheating temperature may be the preheating time.

The preheating method for the aqueous formaldehyde solution is not specifically limited. For example, in the case of production according to a continuous system, there may be employed a preheating method where an aqueous formaldehyde solution is fed into a preheating tube previously heated up to a predetermined preheating temperature and preheated therein, before the aqueous formaldehyde solution is brought into contact with an α-olefin. Regarding the material of the preheating tube, preferably, one that may not be corroded by an aqueous formaldehyde solution is used.

In the present invention, before the step of bringing an α-olefin into contact with an aqueous formaldehyde solution (contact step), if desired, the α-olefin may also be preheated. As described above, the reaction of an α-olefin and formaldehyde is preferably carried out under a high-temperature condition at 150° C. or higher and for a short period of time. Preheating the α-olefin to be reacted with formaldehyde is preferred since the temperature inside the reaction system can be rapidly increased after the contact between the α-olefin and formaldehyde and since the reaction can be attained more efficiently.

In the case where the α-olefin is preheated, the preheating temperature is preferably 70° C. or higher, more preferably 70 to 380° C., even more preferably 120 to 350° C., still more preferably 150 to 320° C., and especially preferably 180 to 280° C. When the preheating temperature is 70° C. or higher, the reaction can be efficiently carried out with ease, and when the temperature is 380° C. or lower, the raw materials can be prevented from decomposing.

The preheating temperature for the α-olefin may be lower than the temperature in the reaction between the α-olefin and formaldehyde, but may also be a temperature during the reaction or higher.

The preheating time and the preheating method for the α-olefin as well as preferred embodiments thereof may be the same as those in the case of preheating the above-mentioned aqueous formaldehyde solution.

Before the contact step, the alcohol having 3 to 10 carbon atoms may also be preheated. In the case where the alcohol having 3 to 10 carbon atoms is preheated, at least one method selected from the group consisting of (1) a method of preheating the alcohol having 3 to 10 carbon atoms by itself, (2) a method of previously preparing a mixture of an α-olefin and an alcohol having 3 to 10 carbon atoms and preheating the mixture, or (3) a method of previously preheating an aqueous formaldehyde solution and an alcohol having 3 to 10 carbon atoms and preheating the mixture may be employed. From the viewpoint of productivity, the method (2) or (3) is preferred, and from the viewpoint of productivity, prevention of formaldehyde decomposition and heating efficiency, the method (2) is more preferred.

In the case where the method (1) or (2) is employed, the preferred preheating temperature is the same as the preheating temperature for the α-olefin, and in the case where the method (3) is employed, the preferred preheating temperature is the same as the preheating temperature for the aqueous formaldehyde solution.

In the present invention, before the step of bringing an α-olefin into contact with an aqueous aldehyde solution (contact step), more favorably, the aqueous formaldehyde solution is preheated at 30 to 220° C., preferably 70 to 190° C., and the mixture of the α-olefin and the alcohol having 3 to 10 carbon atoms is preheated at 70° C. or higher, preferably 70 to 380° C.

<Contact Step>

The production method of the present invention includes a step of bringing an α-olefin into contact with an aqueous formaldehyde solution in the presence of an alcohol having 3 to 10 carbon atoms (contact step). After preheated in the manner as above, an α-olefin is brought into contact with an aqueous formaldehyde solution in the presence of an alcohol having 3 to 10 carbon atoms to thereby make the α-olefin reacted with formaldehyde, and accordingly, the reaction runs on efficiently and a γ,δ-unsaturated alcohol can be produced at high yield and good productivity.

Examples of the method of bringing an α-olefin into contact with an aqueous formaldehyde solution in the presence of an alcohol having 3 to 10 carbon atoms include the following:

(I) A method of bringing an α-olefin, an aqueous formaldehyde solution and an alcohol having 3 to 10 carbon atoms into contact with each other all at the same time.

(II) A method of bringing a mixture of an α-olefin and an alcohol having 3 to 10 carbon atoms into contact with an aqueous formaldehyde solution.

(III) A method of bringing an α-olefin into contact with a mixture of an aqueous formaldehyde solution and an alcohol having 3 to 10 carbon atoms.

From the viewpoint of productivity, the method (II) or (III) is preferred, and in consideration of productivity, prevention of formaldehyde decomposition and heating efficiency, the method (II) is more preferred.

In the case where the contact step is carried out in a continuous mode, for example, according to the method (I), an α-olefin, an aqueous formaldehyde solution and an alcohol having 3 to 10 carbon atoms are fed to individual preheating tubes each preheated up to a desired preheating temperature and preheated therein, and then joined at the outlets of the preheating tubes. According to the method (II), a mixture of an α-olefin and an alcohol having 3 to 10 carbon atoms, and an aqueous formaldehyde solution are fed to individual preheating tubes each preheated up to a desired preheating temperature and preheated therein, and then the mixture and the aqueous formaldehyde solution are joined at the outlets of the preheating tubes. According to the method (III), an α-olefin, and a mixture of an aqueous formaldehyde solution and an alcohol having 3 to 10 carbon atoms are fed to individual preheating tubes each preheated up to a desired preheating temperature and preheated therein, and then the α-olefin and the mixture are joined at the outlets of the preheating tubes.

In the case where the contact step is carried out in a continuous mode, the molar ratio of the α-olefin, formaldehyde and the alcohol having 3 to 10 carbon atoms may be adjusted by controlling the composition of the raw materials to be fed to the preheating tubes and controlling the flow rate thereof to the preheating tubes.

<Reaction Condition>

The reaction of the α-olefin and formaldehyde is carried out under heat. For example, the joined mixture liquid, which is obtained after the contact step, is directly transferred to a reactor, and the α-olefin and formaldehyde can be reacted under heat in the reactor.

The temperature during the reaction between the α-olefin and formaldehyde (temperature under the heating condition) is preferably 150 to 350° C., more preferably 200 to 340° C., and even more preferably 240 to 330° C. At 150° C. or higher, the reaction speed can be high and the reaction time can be shortened. When the temperature during the reaction is 350° C. or lower, formaldehyde and the produced γ,δ-unsaturated alcohol can be prevented from decomposing, and the yield of the targeted γ,δ-unsaturated alcohol tends to be prevented from lowering.

The reactor to be used for the reaction between the α-olefin and formaldehyde may be previously heated up to a desired reaction temperature, which, however, does not apply to the case where the preheating temperature of the α-olefin and the alcohol having 3 to 10 carbon atoms to be brought into the contact step is a temperature not lower than the reaction temperature. For example, in the case where an α-olefin and an alcohol having 3 to 10 carbon atoms are preheated at a temperature not lower than the reaction temperature and then the contact step is carried out, a method of transferring the mixture liquid obtained after the contact step to a reactor having a heating means and then reacting the components therein may be employed. Such a reaction is also contained in the scope of the reaction under a heating condition according to the present invention.

The reaction time may be appropriately set depending on the reaction time, but in general, the reaction may finish in 1 to 60 minutes. Accordingly, even in the case where the reaction is carried out in a continuous mode, the reaction time (the residence time of the mixture liquid in the reactor after the contact step) is preferably within a range of 1 to 60 minutes, more preferably 3 to 40 minutes.

The reaction pressure is a vapor pressure of an α-olefin at the reaction temperature thereof, but in the case where an α-olefin that may be in a critical condition at a predetermined temperature or higher is used, preferably, the pressure is controlled as needed. The reaction pressure is preferably 3.0 to 50.0 MPa, more preferably 3.0 to 30.0 MPa, even more preferably 5.0 to 30.0 MPa, and especially preferably 10.0 to 30.0 MPa.

When the reaction pressure is not lower than the vapor pressure of an α-olefin at the reaction temperature thereof, the concentration of the α-olefin in the reaction liquid can be high to increase the selectivity of γ,δ-unsaturated alcohol, and when the reaction pressure is higher, the reaction speed and the selectivity of γ,δ-unsaturated alcohol tend to be higher. When the reaction pressure is controlled to be 50.0 MPa or less, the construction cost for pressure-tight facilities can be reduced and the danger of reactor disruption may tend to lower.

Preferably, for the reaction, a reactor capable of controlling the reaction temperature, the reaction time and the reaction pressure as mentioned above is used. The reaction may be carried out in any method of a batch system, a semibatch system or a continuous system. Preferably, the reaction is carried out according to a continuous system in which the formaldehyde conversion ratio is high and the reaction selectivity and the yield of γ,δ-unsaturated alcohol are high.

Specific and preferred embodiments of the continuous reaction are as follows. After the preheating and the contact step are carried out according to the above-mentioned method, the mixture liquid obtained after the contact step and containing an α-olefin, an aqueous formaldehyde solution and an alcohol having 3 to 10 carbon atoms in a predetermined ratio is fed to a reactor heated up to a predetermined reaction temperature, at such a flow rate that the residence time of the mixture liquid in the reactor could be a predetermined residence time therein. While the reaction pressure is kept so controlled that the outlet pressure of the condenser tube connected to the outlet of the reactor could be kept at a predetermined pressure, the mixture liquid is kept to remain in the reactor for a predetermined residence time and reacted therein, and then the reaction liquid is continuously discharged out of the outlet of the reactor. In the case where an α-olefin remains in the obtained reaction liquid, preferably, the α-olefin is partitioned and is again used as a raw material.

In the case where the α-olefin and the alcohol having 3 to 10 carbon atoms are preheated at a temperature not lower than the reaction temperature, a method in which, after the above-mentioned contact step, the mixture liquid obtained after the contact step is fed to a reactor having a warming means and is reacted therein is also employable.

EXAMPLES

The present invention is hereunder specifically described with reference to Examples, but it should be construed that the present invention is by no means limited by these Examples.

The reaction liquid in each Example was analyzed through gas chromatography (GC) under the following conditions.
<Gas Chromatography Analysis Conditions>
Apparatus: GC-14A (manufactured by Shimadzu Corporation)
Column: G-300 (inside diameter 1.2 mm×length 20 m, film thickness 2 μm), manufactured by Chemicals Evaluation and Research Institute, Japan
Detector: Hydrogen flame ionization detector (FID)
Carrier gas: Helium (260 kPa)
Carrier gas flow rate: 10 mL/min
Column temperature: 80° C.→Temperature rise at 5° C./min→Held at 210° C. for 4 minutes
Inlet temperature: 220° C.
Detector temperature: 220° C.
Sample injection amount: 0.2 μL Example 1

According to the operation mentioned below, isobutene and formaldehyde were reacted to produce a γ,δ-unsaturated alcohol, 3-methyl-3-buten-1-ol (IPEA). During the production process, each operation was carried out while the pressure inside the reaction system was kept at 200 kg/cm$^2$ (19.6 MPa).

An aqueous solution of 50 mass % formaldehyde (raw material liquid 1A) was fed into a stainless reactor tube (preheating tube 1) preheated at 80° C. and having an inner diameter of 2 mm and a length of 125 mm (inner volume 0.4 mL) at 4.7 mL/hr and preheated therein. On the other hand, a mixture solution of 55.8 mass % of isobutene and 44.2 mass % of tert-butyl alcohol (raw material liquid 2A) was fed into a stainless reactor tube (preheating tube 2) at room temperature (25° C.) having an inner diameter of 2 mm and a length of 1465 mm (inner volume 4.6 mL) at 55.3 mL/hr. The amount of isobutene used relative to 1 mol of formaldehyde was 5 mol, and the amount of tert-butyl alcohol used was 3 mol.

At the outlets of the preheating tubes, the raw material liquid 1A and the raw material liquid 2A were joined and contacted together, and the obtained mixture liquid was immediately fed to a stainless reaction tube (reactor) preheated at 280° C. and having an inner diameter of 2 mm and a length of 1590 mm (inner volume 5 mL) so that isobutene and formaldehyde were reacted in the reactor. The residence time of the each raw material liquid in the preheating tube was 5 minutes, and the residence time of the mixture liquid in the reactor was 5 minutes. The outlet of the reactor was connected to a condenser tube having an inner diameter of 2 mm and a length of 2,000 mm, and while the outlet pressure of the condenser tube was kept at 200 kg/cm² (19.6 MPa), the reaction liquid was made to flow out. The obtained reaction liquid was analyzed through GC under the above-mentioned conditions, and the conversion ratio of formaldehyde was 88.1%, and the selectivity based on the formaldehyde equivalent of the targeted product γ,δ-unsaturated alcohol, 3-methyl-3-buten-1-ol (IPEA) was 84.5%. The production conditions and the results of analysis are shown in Table 1.

Example 2

A mixture solution (raw material liquid 1B) of an aqueous solution of 50 mass % formaldehyde and tert-butyl alcohol at a ratio of 21.3/78.7 (by mass) was fed into a stainless reactor tube (preheating tube 1) preheated at 80° C. and having an inner diameter of 2 mm and a length of 670 mm (inner volume 2.1 mL) at 25.4 mL/hr and preheated therein. On the other hand, isobutene (raw material liquid 2B) was fed into a stainless reactor tube (preheating tube 2) at room temperature (25° C.) having an inner diameter of 2 mm and a length of 920 mm (inner volume 2.9 mL) at 34.6 mL/hr. The amount of isobutene used relative to 1 mol of formaldehyde was 5 mol, and the amount of tert-butyl alcohol used was 3 mol.

At the outlets of the preheating tubes, the raw material liquid 1B and the raw material liquid 2B were joined and contacted together, and the obtained mixture liquid was immediately fed to a stainless reaction tube (reactor) preheated at 280° C. and having an inner diameter of 2 mm and a length of 1,590 mm (inner volume 5 mL) so that isobutene and formaldehyde were reacted in the reactor. The residence time of the each raw material liquid in the preheating tube was 5 minutes, and the residence time of the mixture liquid in the reactor was 5 minutes. The outlet of the reactor was connected to a condenser tube having an inner diameter of 2 mm and a length of 2,000 mm, and while the outlet pressure of the condenser tube was kept at 200 kg/cm² (19.6 MPa), the reaction liquid was made to flow out. The obtained reaction liquid was analyzed through GC under the above-mentioned conditions. The production conditions and the results of analysis are shown in Table 1.

Example 3

IPEA was produced according to the same method as in Example 1 except that, in Example 1, the raw material liquid 2A was fed into the preheating tube 2 heated at 80° C. The production conditions and the results of analysis are shown in Table 1.

Example 4

IPEA was produced according to the same method as in Example 1 except that, in Example 1, the raw material liquid 2A was fed into the preheating tube 2 heated at 280° C. The production conditions and the results of analysis are shown in Table 1.

Example 5

IPEA was produced according to the same method as in Example 1 except that, in Example 1, the aqueous solution of 50 mass % formaldehyde (raw material liquid 1A) was fed into the preheating tube 1 heated at 40° C. The production conditions and the results of analysis are shown in Table 1.

Example 6

IPEA was produced according to the same method as in Example 1 except that, in Example 1, the composition of the raw material liquid 2A was changed to a mixture solution (raw material liquid 2C) of 84.1 mass % of isobutene and 15.9 mass % of tert-butyl alcohol, that the amount of isobutene to be used for the reaction relative to 1 mol of formaldehyde was changed to 7 mol and the amount of tert-butyl alcohol to be used was to 1 mol. The production conditions and the results of analysis are shown in Table 1.

Examples 7 and 8

IPEA was produced according to the same method as in Example 1 except that, in Example 1, the temperature of the preheating tube 1 was changed to that shown in Table 1. The production conditions and the results of analysis are shown in Table 1.

Example 9

An aqueous solution of 37 mass % formaldehyde (raw material liquid 1C) was fed into a stainless reactor tube (preheating tube 1) heated at 80° C. and having an inner diameter of 2 mm and a length of 165 mm (inner volume 0.5 mL) at 6.2 mL/hr and preheated therein. On the other hand, a mixture solution of 55.8 mass % of isobutene and 44.2 mass % of tert-butyl alcohol (raw material liquid 2A) was fed into a stainless reactor tube (preheating tube 2) at room temperature (25° C.) having an inner diameter of 2 mm and a length of 1425 mm (inner volume 4.5 mL) at 53.8 mL/hr. The amount of isobutene used for the reaction relative to 1 mol of formaldehyde was 5 mol, and the amount of tert-butyl alcohol used was 3 mol. The others than the above were the same as in Example 1, and according to the method, IPEA was produced. The production conditions and the results of analysis are shown in Table 1.

Example 10

An aqueous solution of 50 mass % formaldehyde (raw material liquid 1A) was fed into a stainless reactor tube (preheating tube 1) heated at 80° C. and having an inner diameter of 2 mm and a length of 80 mm (inner volume 0.3 mL) at 3.0 mL/hr and preheated therein. On the other hand, a mixture solution of 71.6 mass % of isobutene and 28.4 mass % of tert-butyl alcohol (raw material liquid 2D) was fed into a stainless reactor tube (preheating tube 2) at room temperature (25° C.) having an inner diameter of 2 mm and a length of 1515 mm (inner volume 4.8 mL) at 57.0 mL/hr. The amount of isobutene used for the reaction relative to 1 mol of formaldehyde was 10 mol, and the amount of tert-butyl alcohol used was 3 mol. The others than the above were the same as in Example 1, and according to the method, IPEA was produced. The production conditions and the results of analysis are shown in Table 1.

Example 11

An aqueous solution of 50 mass % formaldehyde (raw material liquid 1A) was fed into a stainless reactor tube (preheating tube 1) heated at 80° C. and having an inner diameter of 2 mm and a length of 50 mm (inner volume 0.1 mL) at 1.8 mL/hr and preheated therein. On the other hand, a mixture solution of 61.9 mass % of isobutene and 38.1 mass % of tert-butyl alcohol (raw material liquid 2E) was fed into a stainless reactor tube (preheating tube 2) at room temperature (25° C.) having an inner diameter of 2 mm and a length of 1545 mm (inner volume 4.9 mL) at 58.2 mL/hr. The amount of isobutene used for the reaction relative to 1 mol of formaldehyde was 15 mol, and the amount of tert-butyl alcohol used was 7 mol. The others than the above were the same as in Example 1, and according to the method, IPEA was produced. The production conditions and the results of analysis are shown in Table 1.

Comparative Example 1

IPEA was produced according to the same method as in Example 2 except that, in Example 2, the raw material liquid 1B was fed into the preheating tube 1 at room temperature (25° C.). The production conditions and the results of analysis are shown in Table 1.

Comparative Examples 2 and 3

IPEA was produced according to the same method as in Example 1 except that, in Example 1, the temperature of the preheating tube 1 was changed as in Table 1. The production conditions and the results of analysis are shown in Table 1.

Comparative Example 4

IPEA was produced according to the same method as in Example 9 except that, in Example 9, the raw material liquid 1C was fed into the preheating tube 1 at room temperature (25° C.). The production conditions and the results of analysis are shown in Table 1.

In the Table, iB is isobutene, TBA is tert-butyl alcohol, FA is formaldehyde, IPEA is 3-methyl-3-buten-1-ol, MPEDs is a mixture of 3-methyl-2-pentene-1,5-diol and 3-methylene-pentane-1,5-diol, MDO is 4,4-dimethyl-1,3-dioxane, and MBD is 3-methyl-1,3-butanediol. In the Table, the selectivity is percentage (%) based on the equivalent of formaldehyde.

TABLE 1

| | | | Example | | | | | | | |
|---|---|---|---|---|---|---|---|---|---|---|
| | | | 1 | 2 | 3 | 4 | 5 | 6 | 7 | 8 |
| Production Conditions | Molar Ratio of Raw Materials | iB:TBA:FA | 5:3:1 | 5:3:1 | 5:3:1 | 5:3:1 | 5:3:1 | 7:1:1 | 5:3:1 | 5:3:1 |
| | Preheating Tube 1 | Raw Material Liquid | 1A 50% FA aq. | 1B 50% FA aq. + TBA | 1A 50% FA aq. | 1A 50% FA aq. | 1A 50% FA aq. | 1A 50% FA aq. | 1A 50% FA aq. | 1A 50% FA aq. |
| | | Temperature (° C.) | 80 | 80 | 80 | 80 | 40 | 80 | 120 | 180 |
| | | Residence Time (min) | 5 | 5 | 5 | 5 | 5 | 5 | 5 | 5 |
| | Preheating Tube 2 | Raw Material Liquid | 2A iB + TBA | 2B iB | 2A iB + TBA | 2A iB + TBA | 2A iB + TBA | 2C iB + TBA | 2A iB + TBA | 2A iB + TBA |
| | | Temperature (° C.) | 25 | 25 | 80 | 280 | 25 | 25 | 25 | 25 |
| | | Residence Time (min) | 5 | 5 | 5 | 5 | 5 | 5 | 5 | 5 |
| | Reactor | Temperature (° C.) | 280 | 280 | 280 | 280 | 280 | 280 | 280 | 280 |
| | | Residence Time (min) | 5 | 5 | 5 | 5 | 5 | 5 | 5 | 5 |
| Results of Analysis | FA Conversion Ratio (%) | | 88.1 | 88.3 | 88.7 | 88.9 | 82.3 | 88.1 | 89.1 | 89.4 |
| | Selectivity (%) | IPEA | 84.5 | 84.6 | 85.0 | 85.5 | 82.8 | 84.6 | 83.9 | 84.3 |
| | | MPEDs | 4.2 | 4.0 | 3.6 | 3.7 | 3.2 | 4.1 | 4.0 | 3.3 |
| | | MDO | 0.9 | 0.8 | 0.6 | 0.5 | 0.2 | 0.9 | 0.2 | 0.3 |
| | | MBD | 0.2 | 0.1 | 0.2 | 0.1 | 0.0 | 0.2 | 0.3 | 0.4 |

| | | | Example | | | Comparative Example | | | |
|---|---|---|---|---|---|---|---|---|---|
| | | | 9 | 10 | 11 | 1 | 2 | 3 | 4 |
| Production Conditions | Molar Ratio of Raw Materials | iB:TBA:FA | 5:3:1 | 10:3:1 | 15:7:1 | 5:3:1 | 5:3:1 | 5:3:1 | 5:3:1 |
| | Preheating Tube 1 | Raw Material Liquid | 1C 37% FA aq. | 1A 50% FA aq. | 1A 50% FA aq. | 1B 50% FA aq. + TBA | 1A 50% FA aq. | 1A 50% FA aq. | 1C 37% FA aq. |
| | | Temperature (° C.) | 80 | 80 | 80 | 25 | 280 | 230 | 25 |
| | | Residence Time (min) | 5 | 5 | 5 | 5 | 5 | 5 | 5 |
| | Preheating Tube 2 | Raw Material Liquid | 2A iB + TBA | 2D iB + TBA | 2E iB + TBA | 2B iB | 2A iB + TBA | 2A iB + TBA | 2A iB + TBA |
| | | Temperature (° C.) | 25 | 25 | 25 | 25 | 25 | 25 | 25 |
| | | Residence Time (min) | 5 | 5 | 5 | 5 | 5 | 5 | 5 |
| | Reactor | Temperature (° C.) | 280 | 280 | 280 | 280 | 280 | 280 | 280 |
| | | Residence Time (min) | 5 | 5 | 5 | 5 | 5 | 5 | 5 |
| Results of Analysis | FA Conversion Ratio (%) | | 83.1 | 93.1 | 94.7 | 88.1 | 95.3 | 92.0 | 88.1 |
| | Selectivity (%) | IPEA | 83.6 | 93.5 | 96.0 | 79.9 | 12.0 | 21.9 | 79.6 |
| | | MPEDs | 3.2 | 2.7 | 1.5 | 2.2 | 0.1 | 4.8 | 1.2 |
| | | MDO | 0.9 | 0.2 | 0.2 | 0.9 | 0.1 | 0.5 | 0.9 |
| | | MBD | 1.2 | 0.0 | 0.0 | 4.2 | 0.9 | 28.1 | 5.2 |

INDUSTRIAL APPLICABILITY

According to the present invention, a γ,δ-unsaturated alcohol can be produced at high yield and good productivity. The γ,δ-unsaturated alcohol can be a raw material or intermediate for various organic compounds, and in particular, 3-methyl-3-buten-1-ol is useful as a precursor of isoprene and moreover as a raw material or intermediate for medicines and perfumes.

The invention claimed is:

1. A method for producing a γ,δ-unsaturated alcohol of formula (2):

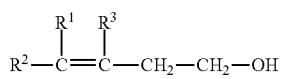
(2)

wherein $R^1$ to $R^3$ each independently represent a hydrogen atom, an alkyl group having 1 to 10 carbon atoms and optionally substituted with a hydroxy group, an alkenyl group having 2 to 10 carbon atoms and optionally substituted with a hydroxy group, or an aryl group having 6 to 12 carbon atoms and optionally substituted with a hydroxy group, provided that $R^1$ and $R^3$ optionally bond to each other to form a ring, through a reaction of an α-olefin of formula (1) and formaldehyde under a heating condition:

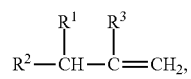
(1)

the method comprising:
contacting the α-olefin with an aqueous formaldehyde solution in the presence of an alcohol having 3 to 10 carbon atoms, wherein the aqueous formaldehyde solution is being subjected to preheating at 30 to 220° C. before contacting the α-olefin with the aqueous formaldehyde solution.

2. The production method according to claim 1, wherein the time for the preheating is less than 30 minutes.

3. The production method according to claim 1, wherein the aqueous formaldehyde solution is subjected to preheating at 70 to 190° C.

4. The production method according to claim 1, wherein the amount of the alcohol having 3 to 10 carbon atoms to be used is from 0.5 to 20 mol relative to 1 mol of formaldehyde in the aqueous formaldehyde solution.

5. The production method according to claim 1, wherein the temperature during the reaction is from 150 to 350° C.

6. The production method according to claim 1, wherein a mixture of the α-olefin and the alcohol having 3 to 10 carbon atoms is brought into contact with the aqueous formaldehyde solution.

7. The production method according to claim 6, wherein before the contacting the α-olefin with the aqueous formaldehyde solution, the mixture is subjected to preheating at 70° C. or higher.

8. The production method according to claim 7, wherein the aqueous formaldehyde solution is subjected to preheating at 70 to 190° C., and the mixture is subjected to preheating at 70 to 380° C.

9. The production method according to claim 1, wherein the reaction is carried out in the absence of a catalyst.

10. The production method according to claim 3, wherein the alcohol having 3 to 10 carbon atoms is at least one selected from the group consisting of n-propanol, isopropyl alcohol, n-butanol, tert-butyl alcohol, isobutyl alcohol, sec-butyl alcohol, n-pentanol, 3-methyl-1-butanol, 2-methyl-2-butanol, hexanol, 3-methyl-3-pentanol, 2-ethylhexanol, heptanol, octanol, isooctanol, 2-ethyl-l-hexanol, nonanol, decanol, cyclopentanol, cyclohexanol, methylcyclohexanol, cycloheptanol, cyclooctanol, cyclodecanol, and benzyl alcohol.

11. The production method according to claim 3, wherein the alcohol having 3 to 10 carbon atoms is at least one selected from the group consisting of isopropyl alcohol, isobutyl alcohol, sec-butyl alcohol, t A-butyl alcohol, 3-methyl- 1 -butanol. and 2-methyl-2-butanol.

* * * * *